(12) United States Patent
Matsunae et al.

(10) Patent No.: US 6,174,935 B1
(45) Date of Patent: Jan. 16, 2001

(54) DENTAL ADHESIVE KIT

(75) Inventors: Kaori Matsunae; Shoji Akahane; Kazuo Hirota, all of Tokyo (JP)

(73) Assignee: GC Corporation, Tokyo (JP)

( * ) Notice: Under 35 U.S.C. 154(b), the term of this patent shall be extended for 0 days.

(21) Appl. No.: 09/213,774

(22) Filed: Dec. 17, 1998

(30) Foreign Application Priority Data

Dec. 24, 1997 (JP) .................................................. 9-366018

(51) Int. Cl.⁷ ........................... A61K 6/083; C08F 20/02; A61C 19/02
(52) U.S. Cl. ........................... 523/118; 523/116; 524/533; 524/558; 526/320; 206/63.5
(58) Field of Search .................................... 523/116, 118; 524/533, 558; 526/320; 206/63.5

(56) References Cited

U.S. PATENT DOCUMENTS

| | | | |
|---|---|---|---|
| 5,908,879 | * 6/1999 | Kawashima et al. | 523/116 |
| 5,925,690 | * 7/1999 | Fuchigami et al. | 524/547 |
| 6,001,897 | * 12/1999 | Dickens | 524/547 |

* cited by examiner

Primary Examiner—Peter A. Szekely

(74) Attorney, Agent, or Firm—Oblon, Spivak, McClelland, Maier & Neustadt, P.C.

(57) ABSTRACT

A dental adhesive kit is disclosed, comprising a combination of:

(i) a self-etching primer comprising (A) from 1.0 to 50% by weight of a methacrylate or acrylate having an acidic group and having at least one unsaturated double bond, (B) from 1.0 to 98% by weight of a water-soluble organic solvent, and (C) from 1.0 to 90% by weight of water; and (ii) a bonding agent comprising (D) from 10 to 90% by weight of a methacrylate or acrylate having neither acidic group nor hydroxyl group and having at least one unsaturated double bond, (E) from 10 to 90% by weight of a methacrylate or acrylate not having an acidic group but having a hydroxyl group and having at least one unsaturated double bond, (F) from 0.1 to 5.0% by weight of a photopolymerization initiator, (G) from 0.1 to 5.0% by weight of a photopolymerization accelerator, and (H) from 1.0 to 60% by weight of a filler.

The dental adhesive kit of the invention is useful for making the adhesive properties of a resin-based adhesive firm and reliable by a simple handling in adhering a dental restorative material to an enamel and a dentin.

3 Claims, No Drawings

DENTAL ADHESIVE KIT

FIELD OF THE INVENTION

The present invention relates to a dental adhesive kit which is used for effectively adhering a dental restorative material to a tooth structure by a simple handling. More particularly, the present invention relates to a dental adhesive kit to be used for making the adhesive properties of a resin-based adhesive firm and reliable by a simple handling in adhering a dental restorative material to an enamel and a dentin.

BACKGROUND OF THE INVENTION

Following the propagation of a composite resin as a dental restorative material, it is required to undergo firm adhesion with safe and confidence between a tooth structure and the composite resin by a simple handling. As adhesion methods which have hitherto been employed, after an acid etching by phosphoric acid or citric acid and so on, a series of handling of water washing→drying→application of a primer→drying →application of an adhesive→polymerization→filling of a composite resin can be exemplified as a representative adhesion method of a restoration. In actual restoration, it is the present state that it takes time to accomplish such handling and that no adhesion with confidence is attained.

Thus, in recent years, adhesion methods for simplifying such complicated handling steps have been being investigated. For example, a new type primer is proposed in, JP-A-3-240,712 and JP-A-7-82,115. In the proposed methods using the new type primer, a tooth is treated with a self-etching primer by which it is said that an etching and a priming can be carried out simultaneously, and after drying, a bonding agent is applied. In other words, a surface of the tooth having a cavity formed therein is treated with the self-etching primer, and the self-etching primer penetrates into the tooth structure while dissolving a smear layer generated upon the cavity formation. Then, a bonding agent is applied, whereby the self-etching primer and the bonding agent are integrated and set to obtain a firm adhesive layer.

However, such kinds of self-etching primers which are commercially available at present need a polymerization catalyst and a polymerization accelerator for setting the polymerizable component in the self-etching primer, and in order to obtain a self-etching primer having good storage stability and stable adhesive capacity, the polymerization catalyst must be separated from the polymerization accelerator. For this reason, self-etching primers which are commercially available at present are constructed by a two-pack type self-etching primer of a polymerization catalyst and a poly-merization accelerator, and the two packs must be mixed with each other before the use. Accordingly, it is not always said that its handling is easy, and there may be a possibility that unstable adhesion is obtained due to a metering error.

SUMMARY OF THE INVENTION

An object of the present invention is to solve the above-described drawbacks of the conventional technologies in adhesion of a dental restorative material to a tooth structure such that the adhesion steps are complicated and take time and that no stable adhesive strength is obtained, whereby clinically satisfactory adhesives have not yet been obtained, and to provide a dental adhesive kit to be used capable of adhering a dental restoration material to a tooth structure firmly and reliably by a simple handling.

We, the present inventors made extensive and intensive investigations in order to achieve the above-described object. As a result, it has been found that when a dental adhesive kit is constructed by a combination of a one-pack type self-etching primer and a one-pack type bonding agent, wherein the one-pack self-etching primer which is free from mixing comprises a methacrylate or acrylate having an acidic group and having at least one unsaturated double bond, a water-soluble organic solvent, and water; and the one-pack bonding agent which is free from mixing comprises a methacrylate or acrylate having neither acidic group nor hydroxyl group and having at least one unsaturated double bond, a methacrylate or acrylate not having an acidic group but having a hydroxyl group and having at least one unsaturated double bond, a photopolymerization initiator, a photopolymerization accelerator, and a filler, firm and reliable adhesion of a dental restoration material to a tooth structure can be obtained by a simple handling, leading to accomplishment of the present invention.

Since the self-etching primers which have hitherto been commercially available need a polymerization initiator and a polymerization accelerator and contain components readily reactive with the polymerization accelerator, such as an acid component and water, these components must be separated from each other taking into account the storage stability and hence, the conventional self-etching primers are provided as a two-pack type self-etching primer which needs intimate mixing before the use. On the other hand, since the self-etching primer in the present invention has a very high affinity with the bonding agent, the polymerizable component in the self-etching primer is readily mixed with the polymerizable component, photopolymerization initiator and photopolymerization accelerator in the bonding agent, thereby enabling one to undergo the photopolymerization. Thus, according to the present invention, an adhesive kit having superior handling and adhesive durability can be provided as a one-pack type self-etching primer and a one-pack type bonding agent, respectively.

When the dentin is treated with the one-pack self-etching primer free from mixing according to the present invention, the (meth)acrylate monomer having an acidic group in the self-etching primer dissolves therein a smear layer as tailings at the time of cavity preparation and penetrates into the dentin while decalcifying the dentin. Then, after drying the water-soluble organic solvent in the self-etching primer, when the one-pack type bonding agent with superior penetration properties is applied onto a tooth surface, the polymerizable component in the self-etching primer having penetrated into the dentin is integrated with the bonding agent, whereby the resin monomer reliably penetrates into the decalcified dentin. At this time, the polymerizable component in the self-etching is uniformly mixed with the photopolymerization initiator and the photopolymerization accelerator in the bonding agent, and the monomer component having thoroughly penetrated into the decalcified dentin is polymerized to form a hybrid layer. Thus, high-strength adhesion is attained.

Also, when the enamel is treated with the one-pack self-etching primer free from mixing according to the present invention, the (meth)acrylate monomer having an acidic group in the self-etching primer dissolves therein a smear layer as tailings at the time of cavity preparation and removes it. At the same time, the (meth)acrylate monomer having an acidic group decalcifies the enamel and penetrates into the enamel while forming unevennesses based on an enamel prism and generating a finer uneven structure based on the crystal structure of hydroxyapatite constituting an enamel on the surface. Then, when the one-pack type bonding agent with superior penetration properties is applied thereonto, the resin monomer is integrated with the polymerizable component in the self-etching primer and polymerized for setting. Thus, firm adhesion is attained.

That is, the dental adhesive kit according to the present invention comprises a combination of:

(i) a self-etching primer comprising (A) from 1.0 to 50% by weight of a methacrylate or acrylate having an acidic group and having at least one unsaturated double bond, (B) from 1.0 to 98% by weight of a water-soluble organic solvent, and (C) from 1.0 to 90% by weight of water; and (ii) a bonding agent comprising (D) from 10 to 90% by weight of a methacrylate or acrylate having neither acidic group nor hydroxyl group and having at least one unsaturated double bond, (E) from 10 to 90% by weight of a methacrylate or acrylate not having an acidic group but having a hydroxyl group and having at least one unsaturated double bond, (F) from 0.1 to 5.0% by weight of a photopolymerization initiator, (G) from 0.1 to 5.0% by weight of a photopolymerization accelerator, and (H) from 1.0 to 60% by weight of a filler.

DETAILED DESCRIPTION OF THE INVENTION

In the dental adhesive kit according to the present invention, the methacrylate or acrylate having an acidic group and having at least one unsaturated double bond, which is contained as the component (A) in the self-etching primer (i) is a methacrylate or acrylate monomer having an acidic group, such as a phosphoric group, a carboxylic group, and a sulfonic group, and having at least one unsaturated double bond.

Examples of methacrylate or acrylate monomers having a phosphoric group and having at least one unsaturated double bond include 2-(meth)acryloyloxyethyl dihydrogenphosphate, bis[2-(meth)acryloyloxyethyl] hydrogenphosphate, 2-(meth) acryloyloxyethylphenyl acid phosphate, 6-(meth) acryloyloxybutyl acid phosphate, 8-(meth)acryloyloxydecyl acid phosphate, and 10-(meth)acryloyloxydecyl dihydrogenphosph-ate.

Examples of methacrylate or acrylate monomers having a carboxylic group and having at least one unsaturated double bond include (meth)acrylic acid, 4-(meth)acryloxyethyl trimellitic acid and an anhydride thereof, 6-(meth) acryloyloxyethyl naphthalene-1,2,6-tricarboxylic acid and an anhydride thereof, 1,4-di(meth)acryloyloxyethyl pyromellitic acid, 2-(meth)acryloyloxyethyl succinic acid, 2-(meth) acryloyloxyethyl maleic acid, 2-(meth)acryloyloxyethyl phthalic acid, 2-(meth)acryloyloxyethyl hexahydrophthalic acid, 11-(meth)acryloyloxy-1,1-undecanedicarboxylic acid, N-(meth) acryloyl-p-aminobenzoic acid, N-(meth)acryloyl-o-aminobenzoic acid, and N-(meth)acryloyl-5-aminosalicylic acid.

Examples of methacrylate or acrylate monomers having a sulfonic group and having at least one unsaturated double bond include 2-sulfoethyl (meth)acrylate and 2-(meth) acrylamido-2-methylpropanesulfonic acid. These methacrylate or acrylate monomers having an acidic group, such as a phosphoric group, a carboxylic group, and a sulfonic group, and having at least one unsaturated double bond can be used singly or in admixture of two or more thereof. Of these are preferred bis[2-(meth) acryloyloxyethyl] hydrogenphosphate, 2-(meth) acryloyloxyethylphenyl acid phosphate, 10-(meth) acryloyloxydecyl dihydrogenphosphate, 4-(meth) acryloxyethyl trimellitic acid and an anhydride thereof, 6-(meth)acryloyloxyethyl naphthalene-1,2,6-tricarboxylic acid and an anhydride thereof, 1,4-di(meth)acryloyloxyethyl pyromellitic acid, and 2-(meth)acrylamido-2-methylpropanesulfonic acid.

A suitable content of the methacrylate or acrylate having an acidic group and having at least one unsaturated double bond is from 1.0 to 50% by weight in the self-etching primer (i). If the content is less than 1.0% by weight, the effects as the self-etching primer, such as dissolution of the smear layer and the decalcification of the tooth structure are low, whereas if it exceeds 50% by weight, the adhesive strength is liable to be lowered.

As the water-soluble organic solvent which is contained as the component (B) in the self-etching primer (i), water-soluble organic solvents capable of making the methacrylate or acrylate having an acidic group and having at least one unsaturated double bond compatible with water and of improving the wettability with the tooth structure are preferred. Particularly preferred examples of the water-soluble organic solvents include ethyl alcohol and acetone. If desired, these water-soluble organic solvents can be used singly or in admixture of two or more thereof. A suitable content of the water-soluble organic solvent is from 1.0 to 98% by weight. If the content is less than 1.0% by weight, since the penetration properties of the self-etching primer into the tooth structure are low, and the drying of the self-etching primer is difficult, a high adhesive strength is not obtained. On the other hand, if it exceeds 98% by weight, since the decalcifying ability of the self-etching primer is low, the adhesive properties are lowered.

As the water which is contained as the component (C) in the self-etching primer (i), ones containing no impurities are used. Suitable examples thereof include distilled water, purified water, ion-exchange water, and deionized water. A suitable content of the water is from 1.0 to 90% by weight. If the content is less than 1.0% by weight, the decalcification of the tooth structure is lowered, and the adhesive properties are lowered. On the other hand, if it exceeds 90% by weight, since the compatibility with the methacrylate or acrylate having an acidic group and having at least one unsaturated double bond is poor, the adhesive properties are lowered.

Next, examples of the methacrylate or acrylate having neither acidic group nor hydroxyl group and having at least one unsaturated double bond, which is contained as the component (D) in the bonding agent (ii) include methyl methacrylate, ethyl methacrylate, isopropyl methacrylate, n-butyl methacrylate, isobutyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis (4-methacryloxydiethoxyphenyl) propane, 2,2-bis(4-methacryloxypolyethoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate, and acrylates corresponding thereto, and methacrylates or acrylates having a urethane bond in the molecule thereof. Examples of the methacrylates or acrylates having a urethane bond in the molecule thereof include di-2-methacryloxyethyl -2,2,4-trimethylhexamethylene dicarbamate and an acrylate corresponding thereto, and compounds represented by the following structural formula:

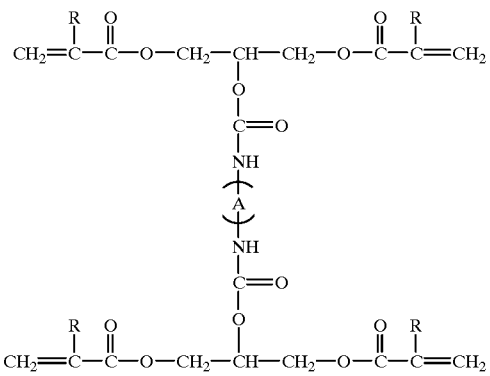

In the above formula, Rs', which may be indentical with or different from each other and each denote H or CH$_3$, and

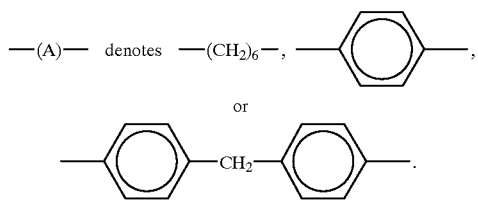

These methacrylates and acrylates are known as dental materials and if desired, can be used singly or in admixture of two or more thereof.

A suitable content of the methacrylate or acrylate having neither acidic group nor hydroxyl group and having at least one unsaturated double bond is from 10 to 90% by weight. If the content is less than 10% by weight, the strength of a material is low, and the photopolymerization properties are lowered. On the other hand, if it exceeds 90% by weight, the affinity is poor, and the adhesive strength is lowered.

Specific examples of the methacrylate or acrylate not having an acidic group but having a hydroxyl group and having at least one unsaturated double bond, which is contained as the component (E) in the bonding agent (ii) include 2-hydroxyethyl methacrylate, 2-hydroxypropyl methacrylate, 2-hydroxy-1,3-dimethacryloxypropane, 2,2-bis[4-(2-hydroxy-3-methacryloxypropoxy) phenyl]propane, and acrylates correspond thereto. Of these compounds are particularly preferred 2-hydroxyethyl methacrylate, 2-hydroxypropyl methacrylate, and 2-hydroxy -1,3-dimethacryloxypropane. A suitable content of the methacrylate or acrylate not having an acidic group but having a hydroxyl group and having at least one unsaturated double bond is from 10 to 90% by weight. If the content is less than 10% by weight, the affinity of the bonding agent to the tooth structure is poor, whereas if it exceeds 90% by weight, the strength of the bonding agent is low, and the adhesive properties are lowered.

If desired, the methacrylate or acrylate not having an acidic group but having a hydroxyl group and having at least one unsaturated double bond can be contained in the self-etching primer (i). In this case, an effect in which the adhesive properties become more stable is observed, and a preferred content of the methacrylate or acrylate not having an acidic group but having a hydroxyl group and having at least one unsaturated double bond in the self-etching primer (i) is from 0.5 to 4.5% by weight.

Examples of the photopolymerization initiator which is contained as the component (F) in the bonding agent (ii) are sensitizing agents such as camphorquinone, benzil, diacetyl, benzyl dimethyl ketal, benzyl diethyl ketal, benzyl di(2-methoxyethyl) ketal, 4,4'-dimethyl benzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2 -chloro-7-trifluoromethylthioxanthone, thioxanthone-10,10-dioxide, thioxanthone-10-oxide, benzoin methyl ether, benzoin isobutyl ether, benzophenone, bis(4-dimethylaminophenyl) ketone, 4,4'-bisdiethylaminobenzophenone, and azide group-containing compounds. These compounds can be used singly or in admixture. A suitable content of the photopolymerization initiator is from 0.1 to 5.0% by weight. If the content is less than 0.1% by weight, reliable polymerization can not be obtained, whereas if it exceeds 5.0% by weight, the physical properties are lowered.

If desired, the photopolymerization initiator can be contained in the self-etching primer (i), and an improvement effect in photocuring characteristics can be expected. In this case, a preferred content of the photopolymerization initiator in the self-etching primer (i) is from 0.1 to 5.0% by weight.

Suitable examples of the photopolymerization accelerator which is contained as the component (G) in the bonding agent (ii) are tertiary amines such as N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate; and barbituric acid derivatives such as barbituric acid, 1,3-dimethylbarbituric acid, 1,3,5-trimethylbarbituric acid, 1,3,5-triethylbarbituric acid, 5-butylbarbituric acid, 1-benzyl-5-phenylbarbituric acid, and 1-cyclohexyl-5-ethylbarbituric acid. A suitable content of the photopolymerization accelerator is from 0.1 to 5.0% by weight. If the content is less than 0.1% by weight, no reliable polymerization is attained, whereas if it exceeds 5.0% by weight, the adhesive properties are lowered. The photopolymerization accelerator is contained only in the bonding agent, and it is not preferable to contain it in the self-etching primer.

The thus obtained photopolymerization type bonding agent (ii) achieves the polymerization reaction upon irradiation of active rays such as ultraviolet light or visible rays. Examples of light sources which can be used include various mercury vapor lamps including extra-high pressure, high pressure, medium pressure, and low pressure ones, a chemical lamp, a carbon arc lamp, a metal halide lamp, a fluorescent lamp, a tungsten lamp, a xenon lamp, and an argon laser.

As the filler which is contained as the component (H) in the bonding agent (ii), inorganic fillers are preferred, and a silica powder, and a glass powder (e.g., a barium glass powder, a fluoroaluminosilicate glass powder) are particularly preferred. Further, if desired, fillers processed with a surface-treating material such as a silane coupling agent can be used. A suitable content of the filler is in a range of from 1.0 to 60% by weight. If the content is less than 1.0% by weight, since the liquid viscosity of the bonding agent is low, the handling property is poor, whereas if it exceeds 60% by weight, the penetration of the bonding agent into the tooth structure is poor, and the adhesive properties are lowered.

In addition, if desired, a polymer not having an acidic group in the molecule thereof can be contained in the bonding agent (ii). Examples of the polymer not having an acidic group in the molecule thereof include poly(methyl acrylate), poly(methyl methacrylate), poly(ethyl acrylate), poly(ethyl methacrylate), poly(isobutyl acrylate), poly(isobutyl methacrylate), poly(n-butyl acrylate), poly(n-butyl methacrylate), and copolymers comprising a combination thereof. Of these compounds are preferred poly(methyl methacrylate), poly(ethyl methacrylate), and a methyl methacrylate/ethyl methacrylate copolymer because they are effective for improving the adhesive properties. A suitable concentration thereof is from 0.5 to 10% by weight to the whole of the bonding agent. If the concentration is less than 0.5% by weight, no improvement in the adhesive properties is found, whereas if it exceeds 10% by weight, the viscosity of the bonding agent is so high that the handling property and storage stability are poor and that the monomer hardly penetrates into the tooth structure, whereby the adhesive properties are lowered.

Besides, if desired, as a matter of course, small amounts of a ultraviolet light absorbent, a coloring agent, a polymerization inhibitor, etc. can be added in the self-etching primer (i) or the bonding agent (ii).

The dental adhesive kit according to the present invention is explained in more detail with reference to the following Examples, but it is not to be construed that the invention is limited thereto.

EXAMPLE 1

Preparation of Self-Etching Primer

A one-pack type self-etching primer was prepared by mixing and dissolving 20% by weight of 2-(meth) acryloyloxyethyl dihydrogenphosphate, 30% by weight of distilled water, and 50% by weight of ethyl alcohol.

Preparation of Bonding Agent

A one-pack type bonding agent was prepared by mixing and dissolving 50% by weight of 2-hydroxy methacrylate, 7% by weight of triethylene glycol dimethacrylate, 30% by weight of di-2-methacryloxyethyl-2,2,4-trimethylhexamethylene dicarbamate, 1.0% by weight of camphorquinone, 2.0% by weight of isoamyl 4-dimethylaminobenzoate, and 10% by weight of a barium glass powder.

Using the thus prepared self-etching primer and bonding agent, the adhesive strength and fitness state were tested according to the following methods. The compounding compositions, compound amounts and results are shown in Table 1.

Measurement of Adhesive Strength

1. With respect to a surface of fresh five bovine front teeth, an enamel and a dentin were exposed and polished, respectively by a #600 waterproof polishing paper under pouring water.
2. A fluorocarbon resin-made masking tape provided with an opening having a diameter of 3.0 mm was laminated onto the polished dentin surface or enamel surface to define a surface to be adhered. The thus defined surface to be adhered was applied with the self-etching primer, kept for 30 seconds, and then dried by a low-pressure air. Subsequently, the resulting surface was applied with the bonding agent and irradiated with a light for 20 seconds by means of a dental visible light ray exposure made by GC Corporation (a product name: GC New Light VL-II).
3. Using a silicone rubber mold having a thickness of 2.0 mm, provided with an opening having an inside diameter of 5.0 mm, the surface to be adhered was applied with a photopolymerization type composite resin made by GC Corporation (a product name: Estio LC) and irradiated with a light for 40 seconds by means the above-described dental visible light ray exposure, thereby curing the resin.
4. After immersing a test specimen in water at 37° C. for one day, a acrylic rod was installed in the upper portion of the test specimen, and a tensile adhesion test was carried out at a cross-head speed of 1.0 mm/min. by means of an autograph manufactured by Shimadzu Corporation. From the results of the adhesion measurement against the enamel and dentin, average values as to respective five specimens were obtained, thereby defining the adhesive strength.

Observation of Fitness State

1. A saucer type cavity was formed on a tooth axis surface of a molar taken out from a human being.
2. According to the measurement of adhesive strength as described above, the respectively prepared self-etching primer and bonding agent were applied onto the whole of the tooth surface, and the photopolymerization type composite resin was filled in the cavity, followed by curing.
3. After curing, each of the specimens was kept in water at 37° C. for 24 hours, the central portion of the cavity was horizontally cut perpendicular to the tooth axis, and the cut surface was smoothly finished by means of a #1000 emery paper under pouring water.
4. After bringing the cut surface into light contact with a phosphoric acid solution, a precise replica of the same surface was prepared, and the replica surface was observed by SEM, thereby observing the bonding state between the resin and the dentin.
5. The determination of the fitness state was carried out according to the Sasazakiis method for determining a space between the resin and the dentin (THE JAPANESE JOURNAL OF CONSERVATIVE DENTISTRY, Vol. 28, No. 2, pp. 452–478, 1985). The determination was made by the score evaluation of five grades of from a grade A to a grade E (A: the fitness is superior, and no space is found; B: a very small space is found; C: a space of less than 5 $\mu$m is found; D: a space of from 5 to 10 $\mu$m is found; E: a space of over 10 $\mu$m is found).

EXAMPLES 2 TO 20

Self-etching primers and bonding agent having the compositions and compounding amounts as shown in Table 1 were prepared and tested in the same manner as in Example 1.

COMPARATIVE EXAMPLES 1 TO 8

As comparative examples, self-etching primers and bonding agent not containing the necessary components of the present invention and those having the compositions and compounding amounts as shown in Table 2 but falling outside the scope of the present invention were prepared and tested in the same manner as in Example 1.

TABLE 1

| | Self-etching primer | | Bonding agent | | Adhesive strength* (MPa) | | Fitness state |
|---|---|---|---|---|---|---|---|
| | | | | | Enamel | Dentin | |
| Example 1 | 2-Methacryloyloxyethyl dihydrogenphosphate | 20 wt % | 2-Hydroxyethyl methacrylate | 50 wt % | 16.2 (3.2) | 18.5 (2.8) | A |
| | Distilled water | 30 wt % | Triethylene glycol dimethacrylate | 7 wt % | | | |
| | Ethyl alcohol | 50 wt % | Di-2-methacryloxyethyl-2,2,4-trimethylhexa-methylene dicarbamate | 30 wt % | | | |
| | | | Camphorquinone | 1 wt % | | | |
| | | | Isoamyl 4-dimethylaminobenzoate | 2 wt % | | | |
| | | | Barium glass powder | 10 wt % | | | |
| Example 2 | 2-Methacryloyloxyethylphenyl acid phosphate | 10 wt % | 2-Hydroxyethyl methacrylate | 50 wt % | 15.8 (3.1) | 17.6 (2.2) | A |
| | Distilled water | 60 wt % | Triethylene glycol dimethacrylate | 34 wt % | | | |
| | Acetone | 30 wt % | 2,2-Bis[4-(2-hydroxy-3-methacryloxypropoxy)-phenyl]propane | 10 wt % | | | |
| | | | Camphorquinone | 0.5 wt % | | | |
| | | | N,N-Dimethylaminoethyl methacrylate | 0.5 wt % | | | |
| | | | Silica powder | 5 wt % | | | |
| Example 3 | 6-Methacryloyloxyethyl naphthalene-1,2,6-tricarboxylate | 50 wt % | 2-Hydroxyethyl methacrylate | 10 wt % | 13.3 (4.2) | 14.5 (3.6) | A |
| | Distilled water | 10 wt % | Di-2-methacryloxyethyl-2,2,4-trimethylhexa-methylene dicarbamate | 56 wt % | | | |
| | Acetone | 40 wt % | Camphorquinone | 2 wt % | | | |
| | | | Ethyl 4-dimethylaminobenzoate | 2 wt % | | | |
| | | | Barium glass powder | 30 wt % | | | |
| Example 4 | 4-Methacryloxyethyl trimellitate anhydride | 1 wt % | 2-Hydroxyethyl methacrylate | 30 wt % | 13.5 (4.2) | 18.2 (2.8) | A |
| | Distilled water | 1 wt % | 2-Hydroxy-1,3-dimethacryloxypropane | 52 wt % | | | |
| | Ethyl alcohol | 98 wt % | Di-2-methacryloxyethyl-2,2,4-trimethylhexa-methylene dicarbamate | 10 wt % | | | |
| | | | Camphorquinone | 5 wt % | | | |
| | | | Ethyl 4-dimethylaminobenzoate | 2 wt % | | | |
| | | | Silica powder | 1 wt % | | | |
| Example 5 | 2-Methacryloyloxyethyl dihydrogenphosphate | 20 wt % | 2-Hydroxyethyl methacrylate | 50 wt % | 17.5 (2.9) | 20.2 (2.5) | A |
| | Distilled water | 30 wt % | Triethylene glycol dimethacrylate | 7 wt % | | | |
| | Ethyl alcohol | 49 wt % | Di-2-methacryloxyethyl-2,2,4-trimethylhexa-methylene dicarbamate | 30 wt % | | | |
| | Camphorquinone | 1 wt % | Camphorquinone | 1 wt % | | | |
| | | | Isoamyl 4-dimethylaminobenzoate | 2 wt % | | | |
| | | | Barium glass powder | 10 wt % | | | |
| Example 6 | 2-Methacryloyloxyethyl dihydrogenphosphate | 20 wt % | 2-Hydroxyethyl methacrylate | 50 wt % | 18.2 (1.8) | 21.2 (1.8) | A |
| | 2-Hydroxyethyl methacrylate | 3 wt % | Triethylene glycol dimethacrylate | 7 wt % | | | |
| | Distilled water | 30 wt % | Di-2-methacryloxyethyl-2,2,4-trimethylhexa-methylene dicarbamate | 30 wt % | | | |
| | Ethyl alcohol | 46 wt % | Camphorquinone | 1 wt % | | | |
| | Camphorquinone | 1 wt % | Isoamyl 4-dimethylaminobenzoate | 2 wt % | | | |
| | | | Barium glass powder | 10 wt % | | | |
| Example 7 | 1,4-Dimethacryloyloxyethyl pyromellitic acid | 20 wt % | 2-Hydroxyethyl methacrylate | 50 wt % | 17.4 (2.6) | 20.4 (2.0) | A |
| | 2-Hydroxyethyl methacrylate | 4.5 wt % | 2-Hydroxy-1,3-dimethacryloxypropane | 35 wt % | | | |
| | Distilled water | 40 wt % | Di-2-methacryloxyethyl-2,2,4-trimethylhexa-methylene dicarbamate | 10 wt % | | | |
| | Acetone | 20 wt % | Camphorquinone | 0.5 wt % | | | |
| | Ethyl alcohol | 15.4 wt % | | | | | |

TABLE 1-continued

| | Self-etching primer | | Bonding agent | | Adhesive strength* (MPa) Enamel | Adhesive strength* (MPa) Dentin | Fitness state |
|---|---|---|---|---|---|---|---|
| | | | Camphorquinone | 0.1 wt % | | | |
| | | | N,N-Dimethylaminoethyl methacrylate | 4 wt % | | | |
| Example 8 | 4-Methacryloyloxyethyl trimellitic acid | 10 wt % | Triethylene glycol dimethacrylate | 75 wt % | 15.8 (2.0) | 18.4 (1.9) | A |
| | 1,4-Dimethacryloxyethyl pyromellitic acid | 7 wt % | Di-2-methacryloxyethyl-2,2,4-trimethylhexa-methylene dicarbamate | 10 wt % | | | |
| | 2-Hydroxyethyl methacrylate | 3 wt % | 2-Hydroxyethyl methacrylate | 10 wt % | | | |
| | Distilled water | 35 wt % | Camphorquinone | 0.5 wt % | | | |
| | Acetone | 43 wt % | Methyl dimethylaminobenzoate | 0.5 wt % | | | |
| | Camphorquinone | 2 wt % | Silica powder | 4 wt % | | | |
| Example 9 | 4-Acryloyloxyethyl trimellitate anhydride | 14 wt % | 2-Hydroxyethyl methacrylate | 50 wt % | 16.2 (2.3) | 17.3 (2.2) | A |
| | 2-Hydroxy-1,3-dimethacryloxypropane | 1 wt % | Triethylene glycol dimethacrylate | 7 wt % | | | |
| | Distilled water | 30 wt % | Di-2-methacryloxyethyl-2,2,4-trimethylhexa-methylene dicarbamate | 30.9 wt % | | | |
| | Acetone | 30 wt % | Camphorquinone | 0.1 wt % | | | |
| | Ethyl alcohol | 20 wt % | Isoamyl 4-dimethylaminobenzoate | 2 wt % | | | |
| | Camphorquinone | 5 wt % | Fluoroaluminosilicate glass powder | 10 wt % | | | |
| Example 10 | 2-Methacryloyloxyethyl dihydrogenphosphate | 4.5 wt % | 2-Hydroxyethyl methacrylate | 50 wt % | 16.8 (3.2) | 18.2 (2.6) | A |
| | 2-Hydroxyethyl methacrylate | 0.5 wt % | 2-Hydroxy-1,3-dimethacryloxypropane | 35 wt % | | | |
| | Distilled water | 90 wt % | Di-2-methacryloxyethyl-2,2,4-trimethylhexa-methylene dicarbamate | 10 wt % | | | |
| | Ethyl alcohol | 4.9 wt % | Camphorquinone | 0.5 wt % | | | |
| | Camphorquinone | 0.1 wt % | N,N-Dimethylaminoethyl methacrylate | 0.5 wt % | | | |
| | | | Silica powder | 4 wt % | | | |
| Example 11 | 2-Methacryloyloxyethyl dihydrogenphosphate | 10 wt % | 2-Hydroxyethyl methacrylate | 15 wt % | 15.8 (2.2) | 16.4 (3.1) | A |
| | 2-Hydroxyethyl methacrylate | 4 wt % | Triethylene glycol dimethacrylate | 20 wt % | | | |
| | Distilled water | 30 wt % | 2,2-Bis[4-(2-hydroxy-3-methacryloxypropoxy)-phenyl]propane | 4.8 wt % | | | |
| | Ethyl alcohol | 55.7 wt % | Camphorquinone | 0.1 wt % | | | |
| | Camphorquinone | 0.3 wt % | N,N-Dimethylaminoethyl methacrylate | 0.1 wt % | | | |
| | | | Fluoroaluminosilicate powder | 60 wt % | | | |
| Example 12 | 2-Methacryloyloxyethyl dihydrogenphosphate | 5 wt % | 2-Hydroxyethyl methacrylate | 50 wt % | 16.9 (4.2) | 17.2 (3.5) | A |
| | 2-Hydroxyethyl methacrylate | 4.5 wt % | 2-Hydroxy-1,3-dimethacryloxypropane | 35 wt % | | | |
| | Distilled water | 89 wt % | Di-2-methacryloxyethyl-2,2,4-trimethylhexa-methylene dicarbamate | 10 wt % | | | |
| | Ethyl alcohol | 1 wt % | Camphorquinone | 0.5 wt % | | | |
| | Camphorquinone | 0.5 wt % | N,N-Dimethylaminoethyl methacrylate | 0.5 wt % | | | |
| | | | Silica powder | 4 wt % | | | |
| Example 13 | 6-Methacryloyloxybutyl acid phosphate | 5 wt % | 2-Hydroxypropyl methacrylate | 34 wt % | 15.4 (2.3) | 16.2 (1.9) | A |
| | 4-Methacryloxyethyl trimellitic acid | 15 wt % | Neopentyl glycol dimethacrylate | 38.5 wt % | | | |
| | Distilled water | 30 wt % | Di-2-methacryloxyethyl-2,2,4-trimethylhexa-methylene dicarbamate | 20 wt % | | | |
| | Acetone | 49.7 wt % | Camphorquinone | 1 wt % | | | |
| | Camphorquinone | 0.3 wt % | N,N-Dimethylaminoethyl methacrylate | 5 wt % | | | |
| | | | Silica powder | 1 wt % | | | |
| | | | Polymetnyl methacrylate | 0.5 wt % | | | |
| Example 14 | 6-Methacryloyloxybutyl acid phosphate | 5 wt % | 2-Hydroxyethyl methacrylate | 55 wt % | 18.2 (2.5) | 18.0 (1.8) | A |
| | 4-Methacryloxyethyl trimellitic acid | 15 wt % | 2-Hydroxy-1,3-dimethacryloxypropane | 29 wt % | | | |

TABLE 1-continued

| | Self-etching primer | | Bonding agent | | Adhesive strength* (MPa) Enamel | Adhesive strength* (MPa) Dentin | Fitness state |
|---|---|---|---|---|---|---|---|
| | Distilled water | 30 wt % | Di-2-methacryloxyethyl-2,2,4-trimethylhexa-methylene dicarbamate | 10 wt % | | | |
| | Acetone | 49.7 wt % | Camphorquinone | 0.5 wt % | | | |
| | Camphorquinone | 0.3 wt % | N,N-Dimethylaminoethyl methacrylate | 0.5 wt % | | | |
| | | | Polyethyl methacrylate | 5 wt % | | | |
| Example 15 | 4-Methacryloxyethyl trimellitic acid | 20 wt % | 2-Hydroxyethyl methacrylate | 55 wt % | 17.8 (2.8) | 16.0 (2.0) | A |
| | 2-Hydroxyethyl methacrylate | 3 wt % | 2-Hydroxy-1,3-dimethacryloxypropane | 24 wt % | | | |
| | Distilled water | 30 wt % | Di-2-methacryloxyethyl-2,2,4-trimethylhexa-methylene dicarbamate | 10 wt % | | | |
| | Ethyl alcohol | 46 wt % | Camphorquinone | 0.5 wt % | | | |
| | Camphorquinone | 1 wt % | N,N-Dimethylaminoethyl methacrylate | 0.5 wt % | | | |
| | | | Polyethyl methacrylate | 10 wt % | | | |
| Example 16 | 1,4-Dimethacryloyloxyethyl pyromellitic acid | 20 wt % | 2-Hydroxyethyl methacrylate | 50 wt % | 18.8 (1.9) | 19.2 (2.4) | A |
| | 2-hydroxyethyl methacrylate | 4.5 wt % | Triethylene glycol dimethacrylate | 8 wt % | | | |
| | Distilled water | 40 wt % | Di-2-methacryloxyethyl-2,2,4-trimethylhexa-methylene dicarbamate | 30 wt % | | | |
| | Acetone | 20 wt % | Camphorquinone | 0.5 wt % | | | |
| | Ethyl alcohol | 15.4 wt % | 1-Cyclohexane-5-ethylbarbituric acid | 1 wt % | | | |
| | Camphorquinone | 0.1 wt % | N,N-Dimethylaminoethyl methacrylate | 0.5 wt % | | | |
| | | | Barium glass powder | 10 wt % | | | |
| Example 17 | 1,4-Dimethacryloyloxyethyl pyromellitic acid | 20 wt % | 2-Hydroxypropyl methacrylate | 44 wt % | 17.4 (2.5) | 17.0 (2.8) | A |
| | 2-Hydroxyethyl methacrylate | 4.5 wt % | Triethylene glycol dimethacrylate | 15 wt % | | | |
| | Distilled water | 40 wt % | Di-2-methacryloxyethyl-2,2,4-trimethylhexa-methylene dicarbamate | 20 wt % | | | |
| | Acetone | 20 wt % | Camphorquinone | 0.4 wt % | | | |
| | Ethyl alcohol | 15.4 wt % | Isoamyl 4-dimethylaminobenzoate | 0.6 wt % | | | |
| | Camphorquinone | 0.1 wt % | Fluoroaluminosilicate glass powder | 20 wt % | | | |
| Example 18 | 6-Methacryloyloxybutyl acid phosphate | 5 wt % | 2-Hydroxyethyl methacrylate | 40 wt % | 15.2 (3.8) | 16.4 (4.1) | A |
| | 4-Methacryloxyethyl trimellitic acid | 25 wt % | Triethylene glycol dimethacrylate | 34.4 wt % | | | |
| | Distilled water | 10 wt % | 2,2-Bis[4-(2-hydroxy-3-methacryloxypropoxy)-phenyl]propane | 20 wt % | | | |
| | Acetone | 59.7 wt % | Camphorquinone | 0.2 wt % | | | |
| | Camphorquinone | 0.3 wt % | N,N-Dimethylaminoethylmethacrylate | 0.4 wt % | | | |
| | | | Silica filler | 5 wt % | | | |
| Example 19 | 2-Methacryloyloxyethyl hexahydrophthalic acid | 10 wt % | 2-Hydroxyethyl methacrylate | 5 wt % | 15.8 (2.8) | 17.4 (2.2) | A |
| | 10-Methacryloyloxydecyl hydrogenphosphate | 5 wt % | 2-Hydroxy-1,3-dimethacryloxypropane | 10 wt % | | | |
| | 2-Hydroxyethyl methacrylate | 3 wt % | Triethylene glycol dimethacrylate | 30 wt % | | | |
| | Distilled water | 20 wt % | Di-2-methacryloxyethyl-2,2,4-trimethylhexa-methylene dicarbamate | 34 wt % | | | |
| | Acetone | 61.8 wt % | Camphorquinone | 0.5 wt % | | | |
| | Camphorquinone | 0.2 wt % | Ethyl 4-dimethylaminobenzoate | 0.5 wt % | | | |
| | | | Fluoroaluminosilicate glass | 20 wt % | | | |
| Example 20 | 2-Acrylamido-2-methylpropanesulfonic acid | 15 wt % | 2-Hydroxyethyl methacrylate | 5 wt % | 16.5 (3.2) | 17.2 (2.3) | A |
| | 2-Hydroxyethyl methacrylate | 3 wt % | 2-Hydroxy-1,3-dimethacryloxypropane | 10 wt % | | | |
| | Distilled water | 20 wt % | Triethylene glycol dimethacrylate | 30 wt % | | | |
| | Acetone | 61.8 wt % | Di-2-methacryloxyethyl-2,2,4-trimethylhexa-methylene dicarbamate | 34 wt % | | | |
| | Camphorquinone | 0.2 wt % | | | | | |

TABLE 1-continued

| Self-etching primer | Bonding agent | | Adhesive strength* (MPa) | | Fitness state |
|---|---|---|---|---|---|
| | | | Enamel | Dentin | |
| | Camphorquinone | 0.5 wt % | | | |
| | Ethyl 4-dimethylaminobenzoate | 0.5 wt % | | | |
| | Fluoroaluminosilicate glass | 20 wt % | | | |

*A numeral in the parenthesis shows a standard deviation.

TABLE 2

| | Self-etching primer | | Bonding agent | | Adhesive strength* (MPa) | Fitness state |
|---|---|---|---|---|---|---|
| Comparative Example 1 | 4-Methacryloxyethyl trimellitic anhydride<br>Distilled water<br>Ethyl alcohol | 0.3 wt %<br>5 wt %<br>94.7 wt % | 2-Hydroxyethyl methacrylate<br>Triethylene glycol dimethacrylate<br>2,2-Bis[4-(2-hydroxy-3-methacryloxypropoxy)-phenyl]propane<br>Camphorquinone<br>N,N-Dimethylaminoethyl methacrylate<br>Silica powder | 50 wt %<br>34 wt %<br>10 wt %<br>0.5 wt %<br>0.5 wt %<br>5 wt % | 2.4<br>(1.0) | 5.2<br>(3.0) | D |
| Comparative Example 2 | 2-Methacryloyloxyethyl dihydrogenphosphate<br>2-Hydroxyethyl methacrylate<br>Distilled water<br>Ethyl alcohol | 60 wt %<br>20 wt %<br>20 wt % | 2-Hydroxyethyl methacrylate<br>Triethylene glycol dimethacrylate<br>2,2-Bis[4-(2-hydroxy-3-methacryloxypropoxy)-phenyl]propane<br>Camphorquinone<br>N,N-Dimethylaminoethyl methacrylate<br>Silica powder | 50 wt %<br>34 wt %<br>10 wt %<br>0.5 wt %<br>0.5 wt %<br>5 wt % | 11.5<br>(3.4) | 6.9<br>(4.8) | C |
| Comparative Example 3 | 2-Methacryloyloxyethylphenyl acid phosphate<br>Acetone<br>Camphorquinone | 10 wt %<br>89.8 wt %<br>0.2 wt % | 2-Hydroxyethyl methacrylate<br>Triethylene glycol dimethacrylate<br>2,2-Bis[4-(2-hydroxy-3-methacryloxypropoxy)-phenyl]propane<br>Camphorquinone<br>N,N-Dimethylaminoethyl methacrylate<br>Silica powder | 50 wt %<br>34 wt %<br>10 wt %<br>0.5 wt %<br>0.5 wt %<br>5 wt % | 4.6<br>(2.8) | 5.5<br>(3.0) | C |
| Comparative Example 4 | 4-Methacryloyloxyethyl trimellitate anhydride<br>Distilled water<br>Camphorquinone | 5 wt %<br>94.8 wt %<br>0.2 wt % | 2-Hydroxyethyl methacrylate<br>Triethylene glycol dimethacrylate<br>2,2-Bis[4-(2-hydroxy-3-methacryloxypropoxy)-phenyl]propane<br>Camphorquinone<br>N,N-Dimethylaminoethyl methacrylate<br>Silica powder | 50 wt %<br>34 wt %<br>10 wt %<br>0.5 wt %<br>0.5 wt %<br>5 wt % | 4.8<br>(3.9) | 7.2<br>(2.5) | C |
| Comparative Example 5 | 1,4-Dimethacryloyloxyethyl pyromellitic acid<br>2-Hydroxyethyl methacrylate<br>Distilled water<br>Acetone<br>Ethyl alcohol<br>Camphorquinone | 20 wt %<br>4.5 wt %<br>40 wt %<br>20 wt %<br>15.4 wt %<br>0.1 wt % | 2-Hydroxyethyl methacrylate<br>2-Hydroxy-1,3-dimethacryloxypropane<br>Camphorquinone<br>N,N-Dimethylaminoethyl methacrylate<br>Silica powder | 50 wt %<br>45 wt %<br>0.5 wt %<br>0.5 wt %<br>4 wt % | 10.2<br>(2.2) | 13.5<br>(1.8) | B |
| Comparative Example 6 | 2-Methacryloyloxyethyl dihydrogenphosphate<br>Distilled water<br>Ethyl alcohol<br>Camphorquinone | 20 wt %<br>30 wt %<br>49 wt %<br>1 wt % | Triethylene glycol dimethacrylate<br>Di-2-methacryloxyethyl-2,2,4-trimethylhexa-methylene dicarbamate<br>Camphorquinone<br>Isoamyl 4-dimethylaminobenzoate | 57 wt %<br>30 wt %<br>1 wt %<br>2 wt %<br>10 wt % | 8.6<br>(1.5) | 8.9<br>(2.1) | C |
| Comparative Example 7 | 2-Methacryloyloxyethyl dihydrogenphosphate<br>Distilled water<br>Ethyl alcohol<br>Camphorquinone | 20 wt %<br>30 wt %<br>49 wt %<br>1 wt % | 2-Hydroxyethyl methacrylate<br>Triethylene glycol dimethacrylate<br>Di-2-methacryloxyethyl-2,2,4-trimethylhexa-methylene dicarbamate<br>Camphorquinone<br>Isoamyl 4-dimethylaminobenzoate<br>Barium glass powder | 50 wt %<br>7 wt %<br>40 wt %<br>1 wt %<br>2 wt %<br>10 wt % | 12.2<br>(2.0) | 11.2<br>(1.8) | B |
| Comparative Example 8 | 2-Methacryloyloxyethyl dihydrogenphosphate<br>2-Hydroxyethyl methacrylate | 20 wt %<br>10 wt % | 2-Hydroxyethyl methacrylate<br>Triethylene glycol dimethacrylate | 50 wt %<br>7 wt % | 11.8<br>(2.4) | 12.0<br>(1.9) | B |

TABLE 2-continued

| Self-etching primer | | Bonding agent | | Adhesive strength* (MPa) | Fitness state |
|---|---|---|---|---|---|
| Distilled water | 20 wt % | Di-2-methacryloxyethyl-2,2,4-trimethylhexa-methylene dicarbamate | 30 wt % | | |
| Ethyl alcohol | 49 wt % | | | | |
| Camphorquinone | 1 wt % | Camphorquinone | 1 wt % | | |
| | | Isoamyl 4-dimethylaminobenzoate | 2 wt % | | |
| | | Barium glass powder | 10 wt % | | |

*A numeral in the parenthesis shows a standard deviation.

As is clear from the above-described Examples and Comparative Examples, it was confirmed that by using the dental adhesive kit comprising a combination of a self-etching primer and a bonding agent according the present invention, the adhesive strength of the dental restorative material to any of an enamel and a dentin is high and that the restoration with superior adhesion can be realized by a simple handling. Also, in the observation of the fitness state in a tooth taken out from a human being, it was confirmed that a space in the adhesion interface, which is considered to be a maximum factor of the secondary caries, is not observed at all and that the restoration with superior peripheral sealing properties can be realized.

Accordingly, the dental adhesive kit according to the present invention can adhere a dental restorative material to a tooth structure firmly and reliably a simple handling from the clinical viewpoint and can be provided for stable dental restoration remedy with superior peripheral sealing properties and free from any anxiety of a secondary caries. Thus, the dental adhesive kit according to the present invention is very valuable in contributing to the dental remedy.

While the invention has been described in detail and with reference to specific embodiments thereof, it will be apparent to one skilled in the art that various changes and modifications can be made therein without departing from the spirit and scope thereof.

What is claimed is:

1. A dental adhesive kit comprising a combination of:

(i) a self-etching primer comprising (A) from 1.0 to 50% by weight of a methacrylate or acrylate having an acidic group and having at least one unsaturated double bond, (B) from 1.0 to 98% by weight of a water-soluble organic solvent, and (C) from 1.0 to 90% by weight of water; and (ii) a bonding agent comprising (D) from 10 to 90% by weight of a methacrylate or acrylate having neither acidic group nor hydroxyl group and having at least one unsaturated double bond, (E) from 10 to 90% by weight of a methacrylate or acrylate not having an acidic group but having a hydroxyl group and having at least one unsaturated double bond, (F) from 0.1 to 5.0% by weight of a photopolymerization initiator, (G) from 0.1 to 5.0% by weight of a photopolymerization accelerator, and (H) from 1.0 to 60% by weight of a filler; wherein said self-etching primer (i) contains from 0.1 to 5.0% by weight of a photopolymerization initiator; and wherein said bonding agent (ii) contains from 0.5 to 10% by weight of a polymer not having an acidic group in the molecule thereof.

2. A dental adhesive kit as claimed in claim 1, wherein said self-etching primer (i) is a self-etching primer containing a methacrylate or acrylate not having an acidic group but having a hydroxyl group and having at least one unsaturated double bond.

3. A dental adhesive kit as claimed in claim 2, wherein said self-etching primer (i) is a self-etching primer containing from 0.5 to 4.5% by weight of the methacrylate or acrylate not having an acidic group but having a hydroxyl group and having at least one unsaturated double bond.

* * * * *